United States Patent [19]

Sim

[11] Patent Number: 6,100,237
[45] Date of Patent: Aug. 8, 2000

[54] USE OF DES-ASPARTATE-ANGIOTENSIN I AS AN AGENT FOR THE TREATMENT AND PREVENTION OF NEOINTIMA FORMATION, RESTENOSIS, AND ARTERIOSCLEROSIS

[75] Inventor: Meng Koon Sim, Singapore, Singapore

[73] Assignee: National University of Singapore, Singapore, Singapore

[21] Appl. No.: 09/172,077

[22] Filed: Oct. 14, 1998

[30] Foreign Application Priority Data

Oct. 24, 1997 [SG] Singapore .......................... 9703863-2

[51] Int. Cl.⁷ .................................................. A61K 38/00
[52] U.S. Cl. ............................................................ 514/15
[58] Field of Search ................................................ 514/15

[56] References Cited

U.S. PATENT DOCUMENTS 5,773,415   6/1998   Sim .......................................... 514/15

*Primary Examiner*—Theodore J. Criares
*Attorney, Agent, or Firm*—Birch, Stewart, Kolasch & Birch, LLP

[57] ABSTRACT

The use of des-Aspartate-angiotensin I (Arg-Val-Tyr-Ile-His-Pro-Phe-His-Leu) as an anti-neointima and anti-arteriosclerotic agent was described. The compound, given intravenously attenuates the development of neointima formation in balloon catheter-injured carotid arteries of Sprague Dawley rats. The anti-neointima action was dose-dependent and the maximum effect was obtained with a dose of 10 pmoles/day given 2 days pre- and 13 days post-balloon catheterization. When given orally on a chronic basis at a dose of 0.9 mg/kg/day for 47 weeks, the compound significantly attenuates the development of arteriosclerosis in the spontaneously hypertensive rats. The anti-arteriosclerotic action was not blood pressure dependent.

12 Claims, No Drawings

USE OF DES-ASPARTATE-ANGIOTENSIN I AS AN AGENT FOR THE TREATMENT AND PREVENTION OF NEOINTIMA FORMATION, RESTENOSIS, AND ARTERIOSCLEROSIS

BACKGROUND ART

In a previous patent application (patent application Ser. No.: 9500519-5, Filing Date: May 5, 1995), the use of des-Aspartate-angiotensin I as an anti-cardiac hypertrophic agent was described. In the embodiments shown in the previous patent application, des-Aspartate-angiotensin I, administered either intravenously or orally, significantly and dose-dependently attenuated the cardiac hypertrophy in experimentally-induced cardiac hypertrophic rats. Therefore, the invention in the previous patent was directed to the use of des-Aspartate-angiotensin I as an anti-cardiac hypertrophic agent.

Des-Aspartate-angiotensin I has been shown to act on a specific indomethacin-sensitive subtype of angiotensin receptor (Sim and Chai, Br. J. Pharmacol., 117:1504–1506 (1996)), and to antagonize the pressor (Sim and Radhakrishnan, Eur. J. Pharmacol., 257:R1–R3 (1994)), and hypertrophic (Min and Sim, Asia Pacific J. Pharmacol. 12:S23 (1997)) actions of angiotensin II. As angiotensin II has either a direct or promotive role in the formation of neointima in balloon catheter-injured blood vessels (Osterrieder et al, Hypertension, 18:II-60-II-64 (1991); Daemen et al, Circ. Res., 68:450–456 (1991)), and chronic development of arteriosclerosis in animals and man (Pitt, Eur Heart J. 16 (Suppl K):49–54 (1995); Timmis and Pitt, Br. Heart J. 72 (Suppl):57–60 (1994)), it is possible that des-Aspartate-angiotensin I could, through its anti-angiotensin II actions, prevent or attenuate the formation of neointima in balloon catheter-injured blood vessels and the chronic development of arteriosclerosis in hypertensive animals and humans.

DISCLOSURE OF INVENTION

In experiments designed to study the effect of des-Aspartate-angiotensin I on the formation of neointima in balloon catheter-injured carotid arteries of normotensive rats, the nonapeptide has been found to significantly attenuate the formation of neointima at doses as low as 5 and 10 pmoles per day, given two days pre- to 13 days post-balloon catheterization. In another set of experiments to study the effect of des-Aspartate-angiotensin I on the chronic development of arteriosclerosis in the spontaneously hypertensive rats, the nonapeptide has been found to significantly attenuate the chronic development of arteriosclerosis when the rats were orally administered a daily dose of 0.9 mg/kg body weight (762 nmoles/kg body weight) for 47 weeks (from 5 weeks old to 52 weeks old).

Therefore, the present invention is directed to the use of des-Aspartate-angiotensin I as an agent that prevents the formation of neointima in balloon catheter-injured blood vessels, and as an anti-arteriosclerotic agent. As neointima formation is a process of restenosis (Landzberg et al, Prog. Cardiovasc. Dis., XXXIX:361–398 (1997)), the use of des-Aspartate-angiotensin I is also directed to the prevention and treatment of restenosis resulting from balloon angioplasty.

MODES FOR CARRYING OUT THE INVENTION

In the practice of the method of the present invention, an effective amount of des-Aspartate-angiotensin I or a derivative or salt thereof, or a pharmaceutical composition containing the same, as described below, is administered to a subject, such as a human patient, via any of the usual and acceptable methods known in the art, either singly or in combination with other pharmaceutical agents such as captopril or other angiotensin converting enzyme inhibitors or angiotensin receptor antagonists. The compound or composition can be administered orally, by suppository, or parenterally (e.g. intramuscularly, intravenously, subcutaneously or intradermally), and in the form of either solid or liquid dosage including tablets, suspensions, or solutions, as is discussed in more detail below. The administration can be conducted in single dosage form with continuous therapy or in single dose therapy ad libitum.

Useful pharmaceutical carriers for the preparation of the pharmaceutical compositions hereof can be solids, liquids or mixtures thereof, thus, the compositions can take the form of tablets, pills, capsules, powders, enterically coated or other protected formulations, sustained release formulations, erodible formulations, implantable devices or components thereof, microsphere formulations, solutions, suspensions, elixirs, aerosols and the like.

Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The composition may be subjected to conventional pharmaceutical expedients such as sterilization and may contain conventional pharmaceutical additives such as preservatives, stabilizing agents, wetting or emulsifying agents, salts for adjusting osmotic pressure, buffers and the like. Suitable pharmaceutical carriers and their formulations are described in Martin, "Remington's Pharmaceutical Sciences", $15^{th}$ Ed.; Mack Publishing Co., Easton (1975); see, e.g. pp. 1405–1412 and pp 1461–1487. Such compositions will, in general, contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of consideration including the stage of the disease or condition, the severity thereof, the schedule of administration, the age and physical characteristics of the subject, and so forth. Proper dosages may be established using clinical approaches familiar to the medicinal arts.

Although the initial work was conducted in a rat experimental model, it is expected that the invention can be utilized in various mammals including, but not limited to, mice, rabbits and humans.

EXAMPLE I

Source of Materials

Des-Aspartate-angiotensin I was obtained from Bachem (Dubendorf, Switzerland). Des-Aspartate-angiotensin I can be prepared by techniques well known in the art. Adult Sprague Dawley rats (SD, 250–300 g) were obtained from the Animal Center, National University of Singapore.

Induction of Neointima Formation

SD rats were subjected to left carotid artery injury by the balloon technique according to the method described by Indolfi et al (*Circulation* 92:1230–1235 (1995)). Briefly, rats were anaesthetized with chloral hydrate (40 mg/kg) and a balloon catheter (2F Fogarty, Edwards Laboratories) was introduced through the left external carotid artery into the common carotid artery. The balloon was inflated to a pressure of 2.2 kg/cm$^2$ by compressed carbogen and passed three times (three cycles) along the common carotid artery. This procedure has been demonstrated to remove all endothelium and to produce some loss of medial smooth muscle cells (Clowes and Clowes, *Lab. Invest.*, 49:208–215 (1983)). The catheter was removed, the left external carotid artery was ligated, and the wound was closed. Formation of neointima in the catheter-injured carotid artery occurred and slowed considerably after 14 days (Clowes and Clowes, *Lab. Invest.*, 52:611–616 (1985)). The right common carotid artery was left intact and served as the control artery.

Administration of Des-Aspartate-Angiotensin I

Two days before the balloon catheterization, animals were pre-treated (daily) with various doses of des-Aspartate-angiotensin I (dissolved in saline) The nonapeptide was administered intravenously via an implanted femoral vein catheter. The intravenous administration was carried out using a microinjector which delivered 200 µl of the peptide solution per hour for two hours. Control animals were similarly administered with saline solution instead of the peptide solution. Following the balloon catheterization, animals were similarly administered either the same dose of des-Aspartate-angiotensin I or saline for 13 days.

Morphometric Quantitation of Neointima Formation

On the fourteenth day following balloon catheterization, animals were anaesthetized with chloral hydrate and both the left and right common carotid arteries of each rat were fixed by perfusion at 120 mm Hg with 100 ml of saline followed by 250 ml of 0.1M phosphate buffer (pH 7.4) containing 4% paraformaldehyde and 1% glutaraldehyde through a cannula place in the left ventricle. The carotid arteries were removed, postfixed overnight in 4% paraformaldehyde and processed for paraffin embedment. 10-µ thick sections were prepared and stained with toluidine blue. 20 such sections were cut from the midportion of the artery towards the distal end and used for morphometric evaluation of neointima formation. The area of the medial smooth muscle cells, lumen, and neointima of each section was quantitated morphometrically using an image analysis system consisting of a BX40 light microscope (Olympus, Japan) fitted with a KY-F55B colour video camera (JVC, Japan) and a Pentium 166 MHz/MMX microcomputer (Datamini, Singapore) installed with an Image Pro Plus 3.0 System (Media Cybernetics, USA) for Windows 95™ The area of the medial smooth muscle cells, lumen, and neointima of each section was converted to volume by multiplying by 10 µ (the thickness of the section). The extent of neointima formation was expressed as a % of occlusion of the lumen by the neointima.

Results

The results of the study are summarized in Table 1. Des-Aspartate-angiotensin I has been found to be an effective agent in preventing the formation of neointima resulting from balloon catheterization. The anti-neointima action is dose-dependent and its maximum action is brought about by an i.v. dose of 10 pmoles/day for 15 days (2 days pre- and 13 days post-catheterization). However, it has no significant effect on the medial smooth muscle cells.

TABLE 1

Effects of des-Aspartate-angiotensin I on the development of neointima in balloon catheter-injured rat common carotid arteries

| Dose | % of Lumen Occlusion by Neointima | | Volume of Media ($\mu^3$) |
|---|---|---|---|
| x 10$^6$) | Right artery | Left artery | Left artery |
| Control animals | 0 | 88 ± 8 | 21 ± 1 |
| 5 pmol | 0 | *47 ± 11 | 18 ± 2 |
| 10 pmol | 0 | *24 ± 8 | 19 ± 3 |
| 15 pmol | 0 | *27 ± 8 | 19 ± 2 |

Each value is the mean ± SEM obtained from eighty 10 µ sections (20 from each individual animal) of the common carotid artery. Control animals were animals that underwent balloon catheterization but were given saline instead of the peptide solution. *Significantly different from the control ($p < 0.01$, ANOVA followed by post hoc Student's t-test).

EXAMPLE II

Source of Materials

Des-Aspartate-angiotensin I was obtained from Bachem (Dubendorf, Switzerland). Des-Aspartate-angiotensin I can be prepared by techniques well known in the art. One-month old Wistar Kyoto rats (WKY) and one-month old spontaneously hypertensive rats (SHR) were obtained from the Animal Resources Center, Western Australia.

Chronic Oral Administration of Des-Aspartate-Angiotensin I

Five weeks old WKY and SHR were housed four to a cage. Four SHR and four WKY were orally administered 0.9 mg/kg/day of des-Aspartate-angiotensin I in 0.5 ml of saline daily for 47 weeks. Four SHR and another four WKY served as control animals and were administered 0.5 ml saline solution daily for 47 weeks. The weight of the animals were determined weekly till 12 weeks old, fortnightly till 27 weeks old and monthly till 47 weeks old. The dose of des-Aspartate-angiotensin I was adjusted to match the increase in weight as the animals grew. The dose of 0.9 mg/kg/day was calculated based on the maximum effective oral anti-cardiac hypertrophic dose (250 nmole per rat of average weight of 325 g) in the previous patent.

Morphometric Quantitation of Arteriosclerosis

The blood pressure of the animals was determined by the tail cuff method on the 46th week of treatment. On the 47th week, animals were anaesthetized with chloral hydrate and a 3-cm section (measured from the left renal artery) of the abdominal aorta was removed and fixed in 4% paraformaldehyde and 1% glutaraldehyde. The aorta was processed for paraffin embedment. 10-µ thick sections were prepared and stained with toluidine blue. Fifty such sections, cut from the distal end of the artery, were used for quantitation. The area of the medial smooth muscle cells was quantitated morphometrically as described above. The area was converted to volume by multiplying by 10µ.

Results

The results of the study are summarized in Table 2. There was no significant difference between the systolic pressure of the control and treated animals. Des-Aspartate-angiotensin I has been found to be an effective anti-arteriosclerotic agent. When administered orally at an anti-cardiac hypertrophic dose of 0.9 mg/kg/day for a period of 47 weeks, it significantly attenuated the development of arteriosclerosis in the SHR. The anti-arteriosclerotic action was not blood pressure dependent.

TABLE 2

Effect of des-Aspartate-angiotensin I on the development of arteriosclerosis in the spontaneously hypertensive rat (SHR)

| Animal | Volume of Medial Smooth Muscle Cells ($\mu^3 \times 10^6$) | Blood Pressure (mm Hg) |
|---|---|---|
| Control SHR | 224 ± 3 | 190 ± 35 |
| Treated SHR | *170 ± 12 | 191 ± 8 |
| Control WKY | 121 ± 5 | 132 ± 3 |
| Treated WKY | 127 ± 6 | 134 ± 8 |

Each value is the mean ± SEM obtained from two hundred 10-$\mu$ sections (50 from each individual animal) of the abdominal aorta. *Significantly different from the control SHR ($p < 0.005$, Student's t-test). Des-Aspartate-angiotensin I has no significant effect on the blood pressure taken at the 46th week of treatment, and the animal weight taken at 12, 27 and 47 weeks old (data not shown). It also does not affect the volume of the medial smooth muscle cell of the normotensive WKY.

INDUSTRIAL APPLICABILITY

The industrial applicability of the invention is primarily in the medical or health care industry as an agent for the prevention and treatment of neointima formation, restenosis, and arteriosclerosis arising from whatever causes.

I claim:

1. A method of preventing and treating neointima formation, restenosis, and arteriosclerosis, which comprises:
    administering to a subject in need of treatment an effect amount of des-Aspartate-angiotensin I.

2. A method of preventing and treating neointima formation, restenosis, and arteriosclerosis, which comprises administering to a subject in need of treatment an effective amount of a composition comprising:
    an effective amount of des-Aspartate-angiotensin I; and a pharmaceutically acceptable carrier or diluent.

3. The method according to claim 1, wherein said des-Aspartate-angiotensin I is administered orally.

4. The method according to claim 1, wherein said des-Aspartate-angiotensin I is administered by suppository.

5. The method according to claim 1, wherein said des-Aspartate-angiotensin I is administered parenterally.

6. The method according to claim 1, wherein said des-Aspartate-angiotensin I is administered in the form of a solid dosage.

7. The method according to claim 1, wherein said des-Aspartate-angiotensin I is administered in the form of a liquid dosage.

8. The method according to claim 2, wherein said des-Aspartate-angiotensin I is administered orally.

9. The method according to claim 2, wherein said des-Aspartate-angiotensin I is administered by suppository.

10. The method according to claim 2, wherein said des-Aspartate-angiotensin I is administered parenterally.

11. The method according to claim 2, wherein said des-Aspartate-angiotensin I is administered in the form of a solid dosage.

12. The method according to claim 2, wherein said des-Aspartate-angiotensin I is administered in the form of a liquid dosage.

* * * * *